United States Patent [19]
Nunes et al.

[11] Patent Number: 5,833,639
[45] Date of Patent: Nov. 10, 1998

[54] SHORT LEG WALKER

[75] Inventors: Victor M. Nunes, Cumberland, R.I.; Brian Fitzpatrick, Randolph, Mass.; Jack R. Harkins, Hollis, N.H.

[73] Assignee: Johnson & Johnson Professional, Inc., Raynham, Mass.

[21] Appl. No.: 726,249

[22] Filed: Oct. 4, 1996

Related U.S. Application Data

[60] Provisional application No. 60/008,020, Oct. 27, 1995.

[51] Int. Cl.⁶ ..................................................... A61F 5/00
[52] U.S. Cl. ............................... 602/23; 602/13; 128/882
[58] Field of Search .............................. 602/5, 6, 13, 23, 602/27; 128/882, DIG. 20

[56] References Cited

U.S. PATENT DOCUMENTS

| | | | |
|---|---|---|---|
| 3,552,044 | 1/1971 | Wiele | 36/71 |
| 4,255,202 | 3/1981 | Swan, Jr. | 106/122 |
| 4,414,965 | 11/1983 | Mauldin et al. | 128/87 |
| 4,446,856 | 5/1984 | Jordan | 602/27 |
| 4,572,169 | 2/1986 | Mauldin et al. | 128/80 |
| 5,078,128 | 1/1992 | Grim et al. | 128/83 |
| 5,197,942 | 3/1993 | Brady | 602/5 |
| 5,288,286 | 2/1994 | Davis et al. | 602/6 |
| 5,329,705 | 7/1994 | Grim et al. | 36/88 |
| 5,352,189 | 10/1994 | Schumann et al. | 602/23 |
| 5,370,133 | 12/1994 | Darby et al. | 128/882 |
| 5,399,152 | 3/1995 | Habermeyer et al. | 602/13 X |
| 5,400,529 | 3/1995 | Bell et al. | 36/93 |
| 5,421,874 | 6/1995 | Pearce | 106/122 |
| 5,425,701 | 6/1995 | Oster et al. | 602/23 |
| 5,435,009 | 7/1995 | Schild et al. | 602/13 X |
| 5,577,998 | 11/1996 | Johnson, Jr. et al. | 602/5 |

FOREIGN PATENT DOCUMENTS

WO 94/27529   12/1994   WIPO ............................... A61F 5/04

*Primary Examiner*—Richard J. Apley
*Assistant Examiner*—Denise Pothier

[57] ABSTRACT

There is disclosed a short leg walker comprising a rigid sole and calf shell and an articulated rigid skin and dorsal shell. The shells are padded at some locations with a non-inflatable padding such as foam or a fiber padding and at other locations with an inflatable bladder and a second bladder between the inflatable bladder and the limb of the patient. The second bladder is responsive to deforming pressure exerted on it and will maintain its support of the limb when the pressure is removed.

2 Claims, 7 Drawing Sheets

SHORT LEG WALKER

CROSS REFERENCE TO RELATED APPLICATIONS

This application claims the benefit of U.S. Provisional application Ser. No. 60/008,020, filed Oct. 27, 1995.

FIELD OF THE INVENTION

The present invention relates to orthopedic devices which are employed to immobilize the foot, lower leg and ankle as a substitute for a plaster of Paris or a synthetic orthopedic cast. The present device provides improved support for the limb.

BACKGROUND OF THE INVENTION

Short leg walkers have become more commonly used to immobilize the lower leg, that is, below the knee, of patients who have suffered fractures or other injuries that necessitate the immobilization of that portion of the leg while the injury is healing. Such devices offer advantages to plaster of Paris or synthetic orthopedic casts in that they can be readily removed for examination of the limb and can be reapplied to the patient at little or no expense. Walkers of this type have been constructed with vertical struts with a platform at the base of the struts onto which the foot is supported. The struts were usually padded to provide support for the limb and affixed to the limb with straps of some type. Examples of such devices can be found in U.S. Pat. Nos. 4,414,965; 4,572,169 and 5,352,189. These devices generally employed a foam padding between the strut and the limb of the patient to secure the strut to the patient and provide a support for the patient's limb. U.S. Pat. Nos. 5,329,705 and 5,400,529 disclose walkers which use some type of air bladder to provide the support for the patient in place of the foam that is disclosed in the previously mentioned patents. U.S. Pat. No. 5,329,705 employs the air bladder in the sole of the walker to provide pressure relief areas for the foot. The air bladder also includes foam to provide the cushion. U.S. Pat. No. 5,078,128 also employs both air bladders and foam padding in a walker to provide the cushioning support for the limb of the patient.

U.S. Pat. Nos. 5,370,133 and 5,425,701 disclosed orthopedic bracing devices which employ semi-rigid molded thermoplastic materials in place of struts. These devices also include padding materials to support the limb. The Darby, et al. U.S. Pat. No. 5,370,133 discloses the use of a material called FLOAM™, furnished by TekSource L.C., as a compression pad around the area of the ankle of the wearer of the device.

Although all of these devices provide some support for the patient, there is a desire to provide improved designs for devices of this type to improve the amount of support provided to the patient's limb and also to provide the flexibility of adjustments so that a relatively small number of different sizes or constructions of such devices would fit the largest number of patients who might need the device.

SUMMARY OF THE INVENTION

The present walker provides improved support for the lower limb of the patient and provides the ability to adjust that support in both the anterior-posterior direction and in the medial-lateral direction. The present walker uses multiple air bladders and padding in the upper areas of the walker to support the limb. There are air bladders to support the limb in the anterior-posterior direction and in the medial-lateral direction. The bladders in the anterior-posterior direction or the front to back portions of the walker may be inflated with a single pump to equal pressures. This is also true in the medial-lateral portions or side to side as those bladders may be filled with a single pump to equal pressures. This provides equal support to the patient's limb in each direction. An alternate and preferred arrangement is to have one pump to inflate the medial, lateral and posterior bladders simultaneously to center the limb. A second pump is employed to inflate an interior bladder to support and secure the limb in the anterior-posterior direction.

The support members of the walker are composed of semi-rigid thermoplastic open shell components which overlap each other where they contact to provide an approved fit of the walker to the limb of the patient. In addition, the present walker may employ a quick release buckle or a hook and loop fastener on the strap to secure the walker to the limb of the patient. The semi-rigid shell of the walker is ambidextrous and can be used on either the right or left leg of the patient. This increases the flexibility of the walker and reduces the inventory cost of carrying multiple shells for right and left feet. The walker employs a padded inner sole which is fitted to either the right or left foot of the patient. The padding or inner sole of the walker is substantially smaller in volume than the shell and can readily be maintained in inventory for use with any particular patient. The walker is also adjustable to some extent in its circumference which also reduces the number of sizes which are required to be maintained in any inventory. As previously mentioned, the present walker employs a rigid thermoplastic shell to provide the necessary support for the limb. This rigid shell is made in two parts. The first half shell is designed to support the calf and the foot of a patient and is generally a single piece of thermoplastic material. The second half shell is a first upper part which covers the shin and attached thereto is a second lower part which covers the dorsal or top of the foot of the patient. These separate half shells are constructed so that when fitted together there is an overlap of the upper part of the second shell over the upper portion of the first shell to enclose the calf and shin of the wearer. The lower part of the first shell overlaps the lower or dorsal part of the second shell. This provides an improved fit of the walker as the upper portion covering the shin and the calf can be fitted separately from the portion of the walker that is in contact with the dorsal or top of the foot of the wearer. This can be adjusted separately as the dorsal covering portion of the second shell fits inside the first shell and the fit is much better than if the dorsal covering portion of the second shell fit over the first shell.

DETAILED DESCRIPTION OF THE INVENTION

Figure 1:
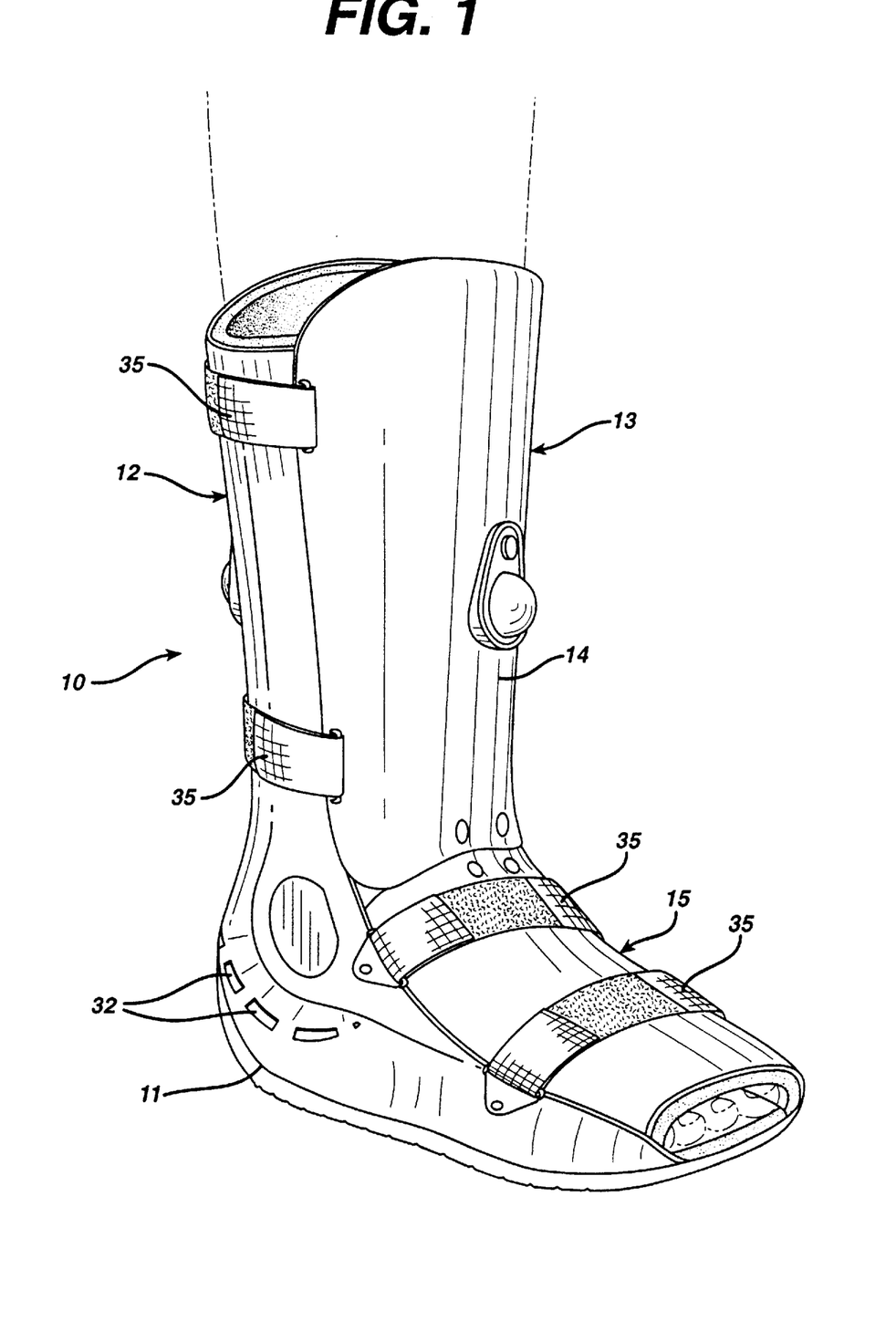
FIG. 1 is an isometric view of the walker of the present invention.
Figure 2:
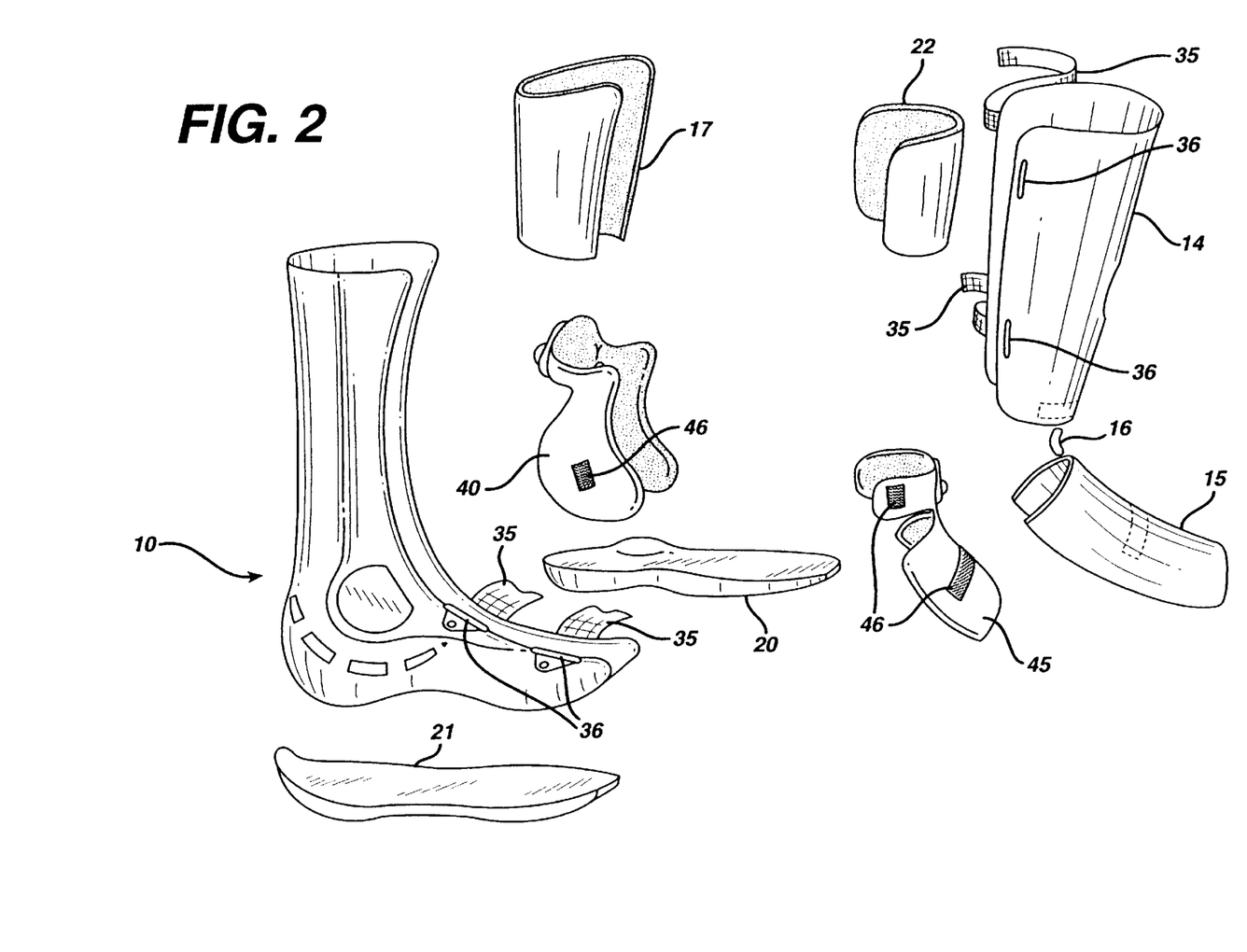
FIG. 2 is an exploded view of the various components of the walker of the present invention.
Figure 3:
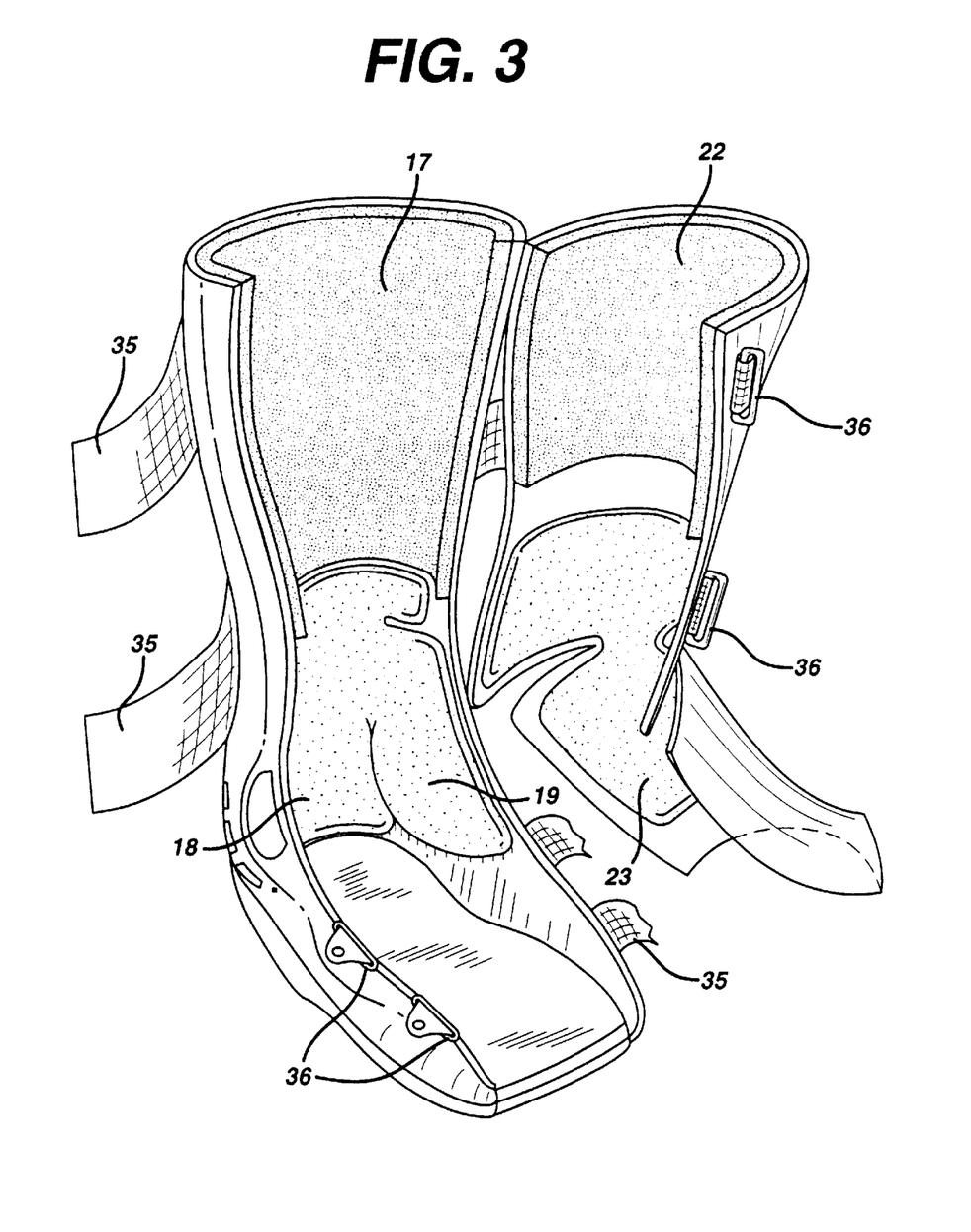
FIG. 3 is an interior view of the walker of the present invention.

The invention can be readily understood by reference to the drawings. FIG. 1, shows an isometric view of the assembled walker of the present invention. The walker comprises a first shell 10, which is preferably a single piece of material and includes a vertical section 12, which will extend from the sole of the foot to the calf of the wearer and a generally horizontal section 11, into which the foot of the wearer would be placed when the boot is worn. There is a second shell 13, which is composed of a shin piece 14, and a connected articulated foot or dorsal covering piece 15. Both the shin covering portion of the shell 14, and the first shell 10, may contain a number of openings 32, to allow the passage of air into the shell. The shell may be composed of any rigid or semi-rigid material, such as a polyethylene, polypropylene, acrylonitrile-butadiene-styrene (ABS) resins or a carbon filled or fiberglass composite material. The two pieces of the second shell portion are joined together with a hinge 16, which is shown in FIG. 2. This hinge allows the second portion or dorsal covering portion 15, of the shell to be drawn in tightly against the upper or dorsal area of the foot of the wearer. The shells have edges 37 around their periphery which overlap or fit within the edges of the opposing shell when the walker is secured on the limb of the wearer. This overlap provides better fitting of the walker to the limb of the wearer.

The walker contains padding in numerous areas in the interior section of the shell, which is best shown in FIG. 2. This padding material includes a non-inflatable foam cushion 17, which is secured to the calf portion of the first shell by adhesively bonding with a pressure sensitive adhesive or with snaps, or with small pieces of a hook and loop fastener. This non-inflatable padding may be a rubber foam, polyurethane foam or other padding material such as fiber padding. There is also inflatable padding such as an achilles tendon padding 18, which is fitted into the rear of the first shell over the area where the rear of the foot, i.e., the achilles tendon area of the patient would contact the shell. This padding is a combination of an air bladder which has a second bladder, i.e., affixed to the exterior surface of the air bladder. The exterior surface is that surface which contacts the limb of the wearer of the walker. The second bladder contains microspheres in a lubricant. This material is furnished by TekSource, L.C., of Salt Lake City, Utah under the name FLOAM™ and is fully described in U.S. Pat. No. 5,421,874 which is incorporated herein by reference. The composite mixture in the FLOAM™ bladder will flow in response to pressure exerted on it but will cease to flow when the pressure is removed. This allows the composite mixture to remain in position supporting the patient's limb. There is also a medial-lateral air bladder which is also composed of an air bladder with a FLOAM™ bladder on the exterior or body contact surface of the air bladder. The air bladder which is attached to the first shell portion 10, and secured to the shell with pressure sensitive adhesive, snaps or hook and loop fasteners.

Fitted into the interior of the bottom of the first shell is an orthotic insert 20, which is configured as either a right or left insert to fit the right or left foot of the user of the walker. The bottom of the shell itself is ambidextrous and can be used on either the wearer's right or left leg. However, it is desirable to provide orthotic support for the foot of the wearer and for that reason the inserts in the present walker are shaped for the right or left foot of the wearer.

On the lower or outer surface of the first portion of the sole of the shell there is provided an outsole 21, which may be a single piece of material as shown in the drawings or which may be two pieces of material, a single piece being preferred. The outsole provides traction for the outer surface of the shell and generally is in a rocker-shape as is common with walkers of this type.

Figure 4:
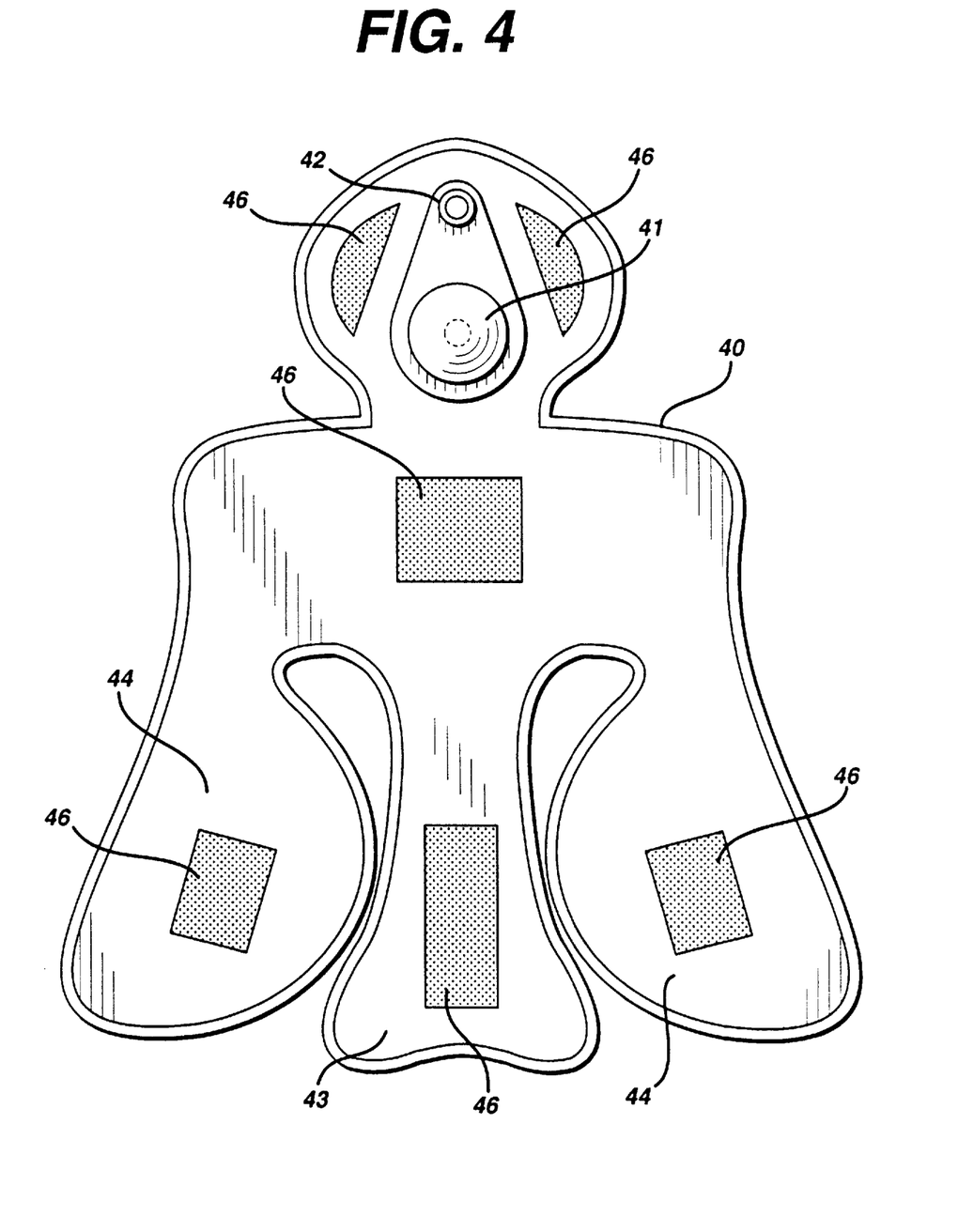
FIG. 4 is a plan view of the rear medial/lateral bladder used in the walker of the present invention.
Figure 5:
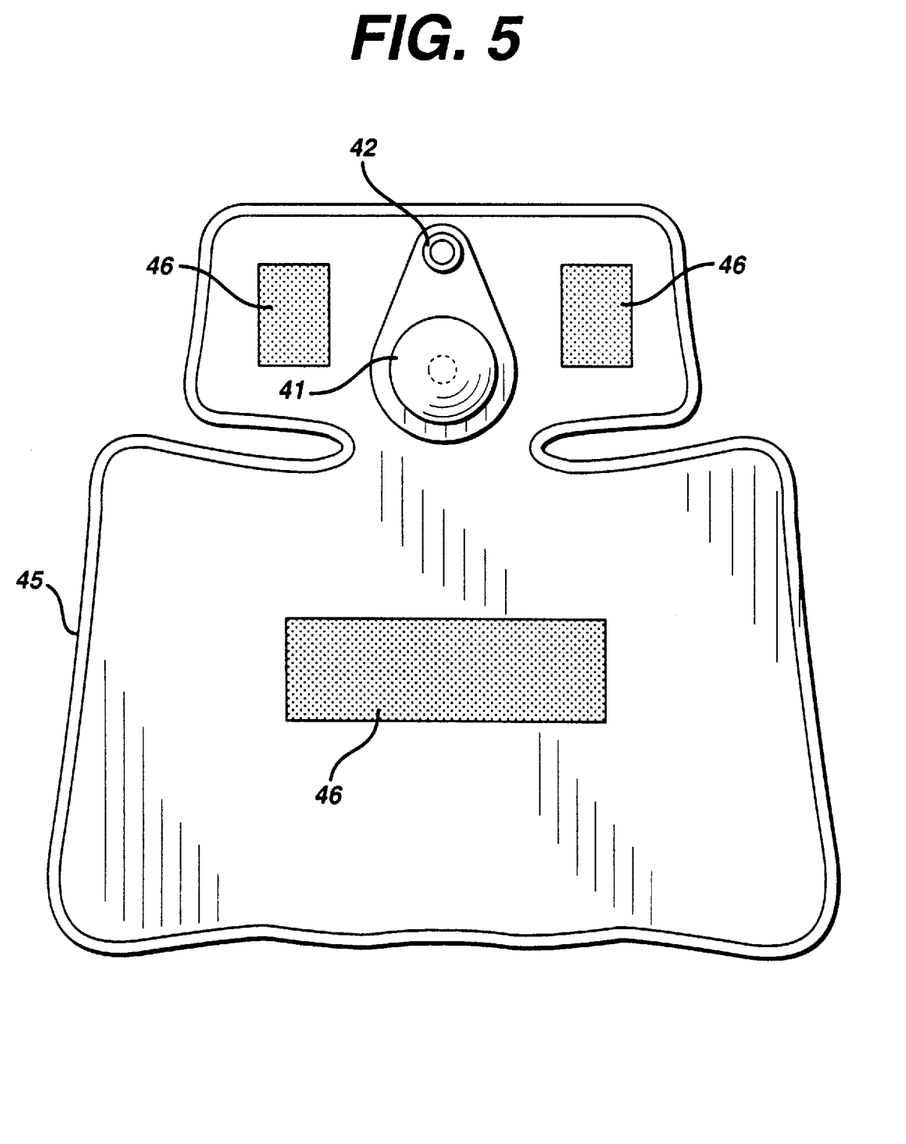
FIG. 5 is a plan view of the front bladder used in the walker of the present invention.
Figure 6:
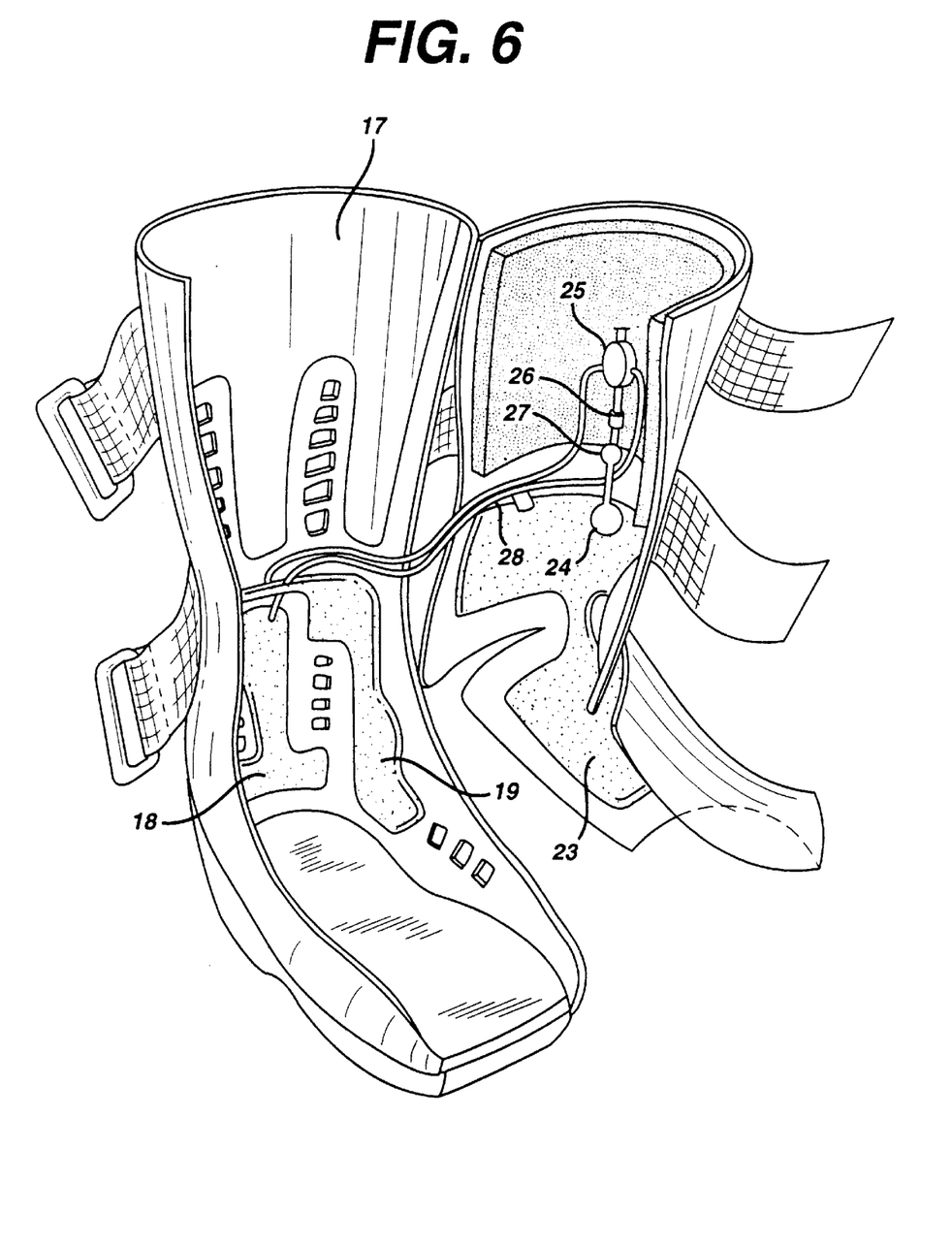
FIG. 6 is an interior view of the walker of the present invention showing an alternate embodiment of the air bladder.
Figure 7:
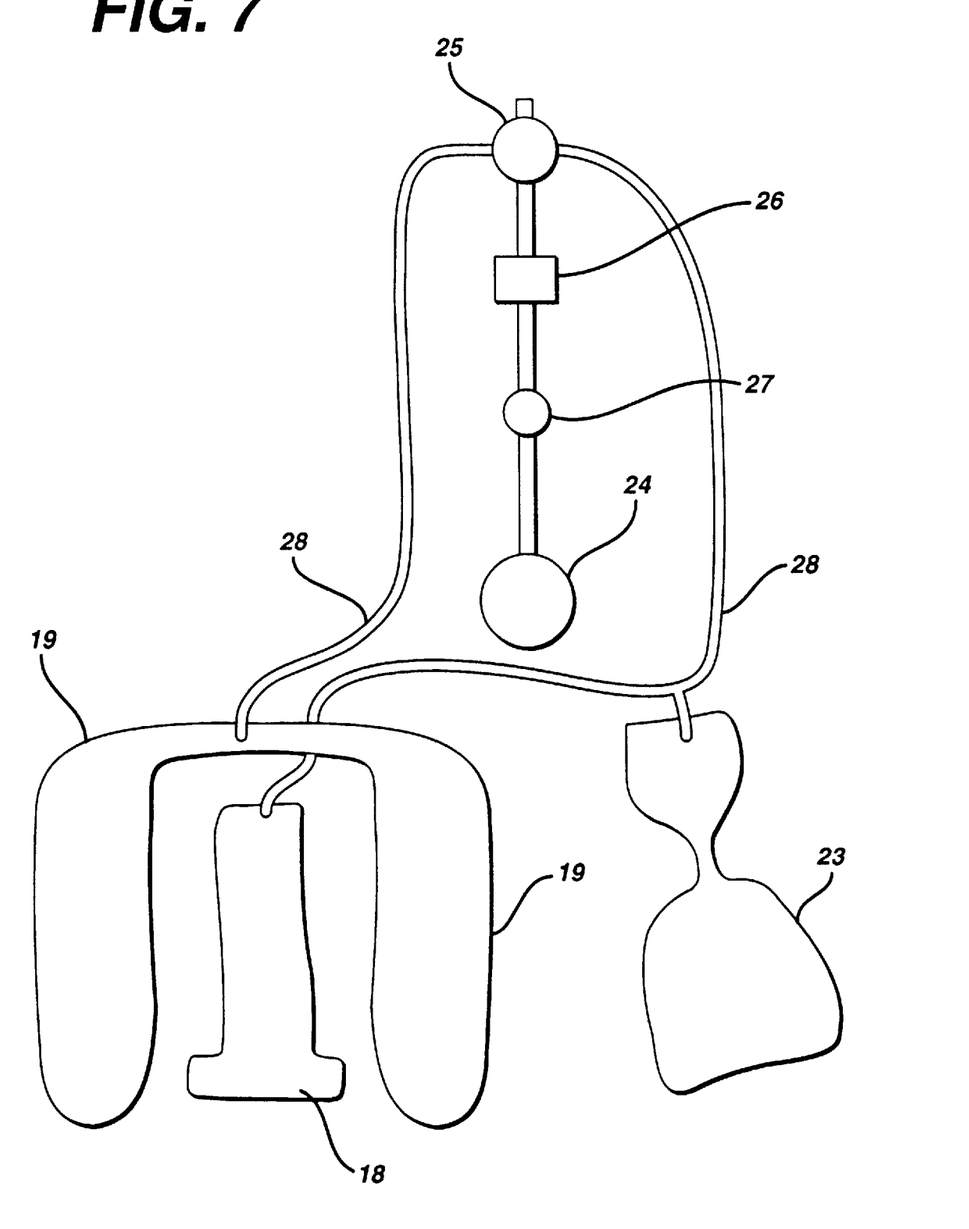
FIG. 7 is a schematic view of the air bladder and pump of the bladder shown in FIG. 6.

In the second shell 13, there is a padding 22, in the upper portion of the shell adjacent which would be in contact with the shin of the patient. This padding may be foam rubber, polyurethane foam or other soft padding material. It is secured to the second portion of the shell in the same manner as the foam padding 17. There is a dorsal padding 23, which covers the top of the foot. This dorsal padding is also a combination of an air bladder and a FLOAM™ bladder and is operably connected on inflation with the achilles or posterior bladder which is secured to the first shell as shown in FIGS. 6 and 7 or is preferably separately inflated as shown in FIGS. 4 and 5. The second shell is configured so that the width of the shin portion is greater than the width of the top portion of the first shell so that the shin portion of the second shell overlaps the calf portion of the first shell when the device is fitted to the wearer.

The dorsal portion of the second shell is dimensioned so that its width is less than the width of the foot portion of the first shell so that the dorsal portion will fit inside the first shell for adjustment and into close contact with the foot of the wearer. The hinge 16, allows the dorsal portion of the second shell to move independently from the shin portion of the shell.

As shown in FIG. 6, there may be employed to inflate the bladders, a series of pumps, valves and tubing which provides and directs the air to the inflatable bladders. There is a manual diaphragm pump 24, which is connected to a three-way or four-way valve 25, through a maximum pressure release valve 26, and a release valve 27. The maximum pressure release valve is set so that there is a maximum pressure which can be applied to the device. The release valve is the normal valve which is used to deflate the air bladders under normal circumstances when the device is to be refitted or to adjust in the bladder. The pump and valves that can be used in the present walker include a Martin Weston low profile pump 1L-500 as the diaphragm pump 24; a Martin Weston clear valve release as the release valve 27; a Smart Products 300 PPB ½ relief or 300 NYB ½ relief as the excessive pressure release valve 26, and a Qasima 99702 four-way stopcock as the valve. The bladders are connected through tubing 28, to the particular bladder or bladders which are to be inflated. A single valve setting will inflate the achilles tender bladder and the dorsal bladder at the same time. This puts equal pressure in the anterior-posterior direction when the bladders are inflated. A second position of the valve inflates the medial-lateral bladders which may be an inter-connected bladder or two bladders with connected tubing so that they will both inflate at the same time. The FLOAM™ bladders 30 and 31 overlie, that is, are the patient contact surfaces of the air bladders 19 and 23.

In the preferred construction of the walker, this is a single air bladder on the rear or posterior portion of the walker which extends to the sides or medial/lateral portion of the walker. This construction of the bladder is illustrated in FIG. 4. The bladder 40 has an attached air pump 41 and a pressure release valve 42. The bladder has a posterior or achilles bladder contact area 43 and medial/lateral bladder contact areas 44. In the preferred construction of the walker, a second bladder of the construction shown in FIG. 5, is in contact with the instep and lower shin of the wearer. This bladder 45 employs a separate air pump 41 and pressure release valve 42. The bladder may have hook and loop fastening elements 46, positioned to contact mating hook and loop fastening elements (not shown) on the interior surface of the shells. The air pumps extend through openings in the shells.

There are a series of straps 35, shown in FIGS. 1, 2 and 6 to secure the walker to the patient. These straps are generally nylon or canvas and may have quick disconnect buckles or hook and loop fasteners. The preferred straps are constructed with hook and loop fasteners at their ends and are secured to the walker through metal guides 36, secured to the edges of the shells.

When in use, the left or right foot is inserted into the base or sole of the walker and the two shells are brought together and the straps are secured so that the shells fit snugly to the leg of the wearer. The valve would then be set for anterior-posterior inflation and the achilles tendon bladder and the dorsal bladder would be inflated. Once these bladders are properly inflated, the valve would be turned to a second position where the medial-lateral bladders would be inflated to securely fit the walker to the patient.

In the preferred embodiment, the posterior medial/lateral bladders would be inflated with the pump on the rear of the walker to position the leg in the walker. The instep bladder would then be inflated with the pump on the front of the walker to complete the positioning of the walker.

What is claimed is:

1. A lower leg immobilizing walker comprising a first semi-rigid open shell having a sole portion and an attached calf and ankle portion and a second open semi-rigid shell comprising a shin portion and an instep portion flexibly connected to the shin portion, said first and second shells adapted to overlap to fit together and surround the lower leg and foot of the wearer, said sole portion having an interior and exterior surface, a soft flexible orthotic insert overlying at least a major portion of the interior surface of the sole portion, an elastomeric sole underlying a major portion of the exterior surface of the sole portion and having a hard exterior surface, a first padding secured to the medial, lateral and posterior interior surfaces of said first shell to provide supporting contact for the calf of the wearer, a second padding secured to an interior surface of the shin portion of the second shell to contact the shin and instep of the wearer, said first and second padding each including an expandable bladder connected to air pumps capable of inflating said bladders and said first and second padding, each including a second bladder containing microspheres in a lubricant on the surface of the expandable bladder facing the limb of the wearer, and multiple straps attached to said shells to secure the first and second shells together and secure said walker to leg of the wearer.

2. The walker of claim 1 in which there is an edge around the periphery of each of the shells and in which the edges of the instep portion of the second shell fit within the edges of the sole portion of the first shell and the edges of the calf portion of the first shell fit within edges of the shin portion of the second shell when the walker is secured to the leg of the wearer.

* * * * *